US010001462B2

(12) United States Patent
Lin et al.

(10) Patent No.: US 10,001,462 B2
(45) Date of Patent: Jun. 19, 2018

(54) METHOD AND SYSTEM FOR DETECTING PESTICIDE RESIDUE IN AGRICULTURAL PRODUCTS USING MASS SPECTROMETRY IMAGING ANALYSIS

(71) Applicant: AGRICULTURAL CHEMICALS AND TOXIC SUBSTANCES RESEARCH INSTITUTE, COUNCIL OF AGRICULTURE, EXECUTIVE YUAN, Taichung (TW)

(72) Inventors: Shao-Kai Lin, Taichung (TW); Wei-Chen Chuang, Taichung (TW)

(73) Assignee: AGRICULTURAL CHEMICALS AND TOXIC SUBSTANCES RESEARCH INSTITUTE, COUNCIL OF AGRICULTURE, EXECUTIVE YUAN, Taichung (TW)

( * ) Notice: Subject to any disclaimer, the term of this patent is extended or adjusted under 35 U.S.C. 154(b) by 0 days. days.

(21) Appl. No.: 15/476,408

(22) Filed: Mar. 31, 2017

(65) Prior Publication Data
US 2017/0284984 A1 Oct. 5, 2017

(30) Foreign Application Priority Data
Apr. 1, 2016 (TW) .............................. 105110624 A

(51) Int. Cl.
G06K 9/00 (2006.01)
G01N 30/72 (2006.01)
(Continued)

(52) U.S. Cl.
CPC ............. G01N 30/72 (2013.01); G01N 30/06 (2013.01); G01N 30/8679 (2013.01)

(58) Field of Classification Search
CPC ..... G01N 30/72; G01N 30/8679; G01N 30/06
See application file for complete search history.

(56) References Cited

U.S. PATENT DOCUMENTS 8,266,197 B1 * 9/2012 Van Benthem ...... G01N 23/223
702/23
2005/0273276 A1 * 12/2005 Szelewski .......... G01N 30/8675
702/30
(Continued)

FOREIGN PATENT DOCUMENTS

CN 103328966 A 9/2013
TW 201512641 A1 4/2015

Primary Examiner — John Strege
(74) Attorney, Agent, or Firm — Muncy, Geissler, Olds & Lowe, P.C.

(57) ABSTRACT

A method and system for detecting pesticide residue in agricultural products. The system includes a chromatographic and mass-spectrometric system and a computer. The system inspects first and second sample solutions prepared from two identical extracts of an agricultural product. The first sample solution includes no additives while the second sample is added with a pesticide standard which is intended to be detected by the system for comparison. The computer compares the mass chromatograms of the first and second sample solutions, and calculate an increased integral area by which the peak of the second sample solution in the second mass chromatogram exceeds the peak of the first sample solution in the first mass chromatogram at the same retention time. As such, the concentration of pesticide residue in the sample can be determined by a ratio between the increased integral area and the concentration of the pesticide standard.

9 Claims, 5 Drawing Sheets

(51) Int. Cl.
    *G01N 30/06*     (2006.01)
    *G01N 30/86*     (2006.01)

(56) References Cited

U.S. PATENT DOCUMENTS

| | | | |
|---|---|---|---|
| 2010/0114514 A1* | 5/2010 | Wang | G01J 3/02 |
| | | | 702/82 |
| 2011/0299066 A1 | 12/2011 | Kusukame et al. | |
| 2013/0289893 A1* | 10/2013 | Kawase | H01J 49/0036 |
| | | | 702/23 |
| 2014/0014833 A1* | 1/2014 | Sekiya | G01N 30/8651 |
| | | | 250/288 |
| 2015/0185153 A1* | 7/2015 | Zhang | G01N 21/65 |
| | | | 356/301 |

* cited by examiner

METHOD AND SYSTEM FOR DETECTING PESTICIDE RESIDUE IN AGRICULTURAL PRODUCTS USING MASS SPECTROMETRY IMAGING ANALYSIS

BACKGROUND OF THE INVENTION

1. Field of the Invention

The present invention relates to a method and system for rapid detection of pesticide residues in agricultural products.

2. Description of the Related Art

It is well-known that a mass spectrometry can be used for pesticide residues analysis. In that system, a mass spectral database with hundreds or thousands of pesticides information should be built up in advance. With this database, any pesticide residue in agricultural products can be identified if its mass spectrum is found to be mated with any of the known pesticides in the mass spectral database. In this method, however, pesticide analytes can merely be identified, but not measured. Moreover, the analytical results of the pesticides may be influenced by the sensitivity of the instrument, types of pesticides and matrix effects of agricultural products. Thus, it is still challenging to perform a quantitative analysis for pesticide residues using the mass spectrometry.

Nowadays, the global agriculture industry uses over a thousand different pesticides for the production of food and foodstuffs. For food safety, in many countries, all food products should be examined to meet standards for pesticide residue limits in foods. To rapid detection of pesticide residues, a QuEChERS method has been readily accepted by many pesticide residue analysts for "pretreatment" of the sample to be analyzed. The name "QuEChERS" is a portmanteau word formed from "Quick, Easy, Cheap, Effective, Rugged, and Safe". This straightforward sample preparation allows for the analysis of hundreds of pesticides at low concentrations with a single extraction. Following the pretreatment, the sample (the extract) is put through a cleanup column prior to analysis by liquid chromatography-mass spectrometry (LC-MS) or gas chromatography-mass spectrometry (GC-MS). During the analysis process, the analysts will have to create a matrix-matched calibration curve for determining the concentration of a substance in an unknown sample by comparing the unknown to a set of standard samples of known concentration. Additionally, the analysts will have to visually observe the mass chromatogram of the unknown sample and check if any peak appears at a specific retention time in the mass chromatogram that corresponds to a known pesticide in the standard sample, in order to identify the pesticide in the unknown sample. Subsequently, the matrix-matched calibration curve is used to determine the concentration of the pesticide in the unknown sample. However, this analytical procedure is quiet complicated and time-consuming. According to statistics, for one single pesticide, it takes about 20 minutes to identify and quantitate. If in terms of hundreds of pesticides, it will take enormous amounts of time.

SUMMARY OF THE INVENTION

Accordingly, it is an object of the present invention to provide a method and system for rapid detection of pesticide residues in agricultural products.

In one aspect, the pesticide residue detection method includes the following steps:

(a). preparing two identical extracts obtained from a sample to be analyzed, and turning one of the two extracts into a first sample solution with no additives, and the other extract to a second, spiked sample solution in which at least one pesticide standard of a known concentration (X) is added;

(b). introducing the first and second sample solutions consecutively into a chromatographic and mass-spectrometric system to create a first mass chromatogram for the first sample solution and a second mass chromatogram for the second, spiked sample solution, wherein a peak of the pesticide standard added in the second, spiked sample solution is to be detected at a retention time as shown in the second mass chromatogram;

c). running an image recognition algorithm to compare the first and second mass chromatograms in order to determine whether a peak appears at the same retention time in the first mass chromatogram, and the peak in the first mass chromatogram has a shape substantially identical or similar to that of the peak of the pesticide standard in the second mass chromatogram, and an intensity slightly smaller than that of the peak of the pesticide standard;

if no, it is determined that the sample contains no pesticide residue of the same kind as the pesticide standard; and if yes, executing an image analysis to calculate an increased integral area (A1), representative for the concentration (X1) of the pesticide standard, by which the peak of the second, spiked sample solution in the second mass chromatogram exceeds the peak of the first sample solution in the first mass chromatogram at the same retention time, and determining a concentration (Y) of a pesticide residue in the sample with the formula:

$$Y=(A2/A1)X$$

where A2 is an integral area of the peak in the first mass chromatogram at the same retention time, A1 is the increased integral area, and X is the concentration of the pesticide standard.

Preferably, the step (c) comprises the following steps:

(1). integrating a peak area of the first sample solution and a peak area of the second, spiked sample solution at the same retention time; and (2). subtracting the peak area of the first sample solution from the peak area of the second, spiked sample solution at the same retention time to get the increased integral area (A1).

In practice, the chromatographic and mass-spectrometric system may be selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS).

In another aspect, the present invention provides a pesticide residue detection method for multiple samples, comprising the following steps:

(a). preparing two identical extracts obtained from a first sample to be analyzed, and turning one of the two extracts into a first sample solution with no additives, and the other extract to a second, spiked sample solution in which at least one first pesticide standard of a known concentration (X1) is added;

(b). preparing another two identical extracts obtained from a second sample to be analyzed, and turning one of the two extracts into a first sample solution with no additives, and the other extract to a second, spiked sample solution in which at least one second pesticide standard of a known concentration (X2) is added;

(c). introducing the first and second sample solutions of the first sample consecutively into a chromatographic and mass-spectrometric system to create a first mass chromatogram for the first sample solution and a second mass chromatogram for the second, spiked sample solution, wherein a peak of the first pesticide standard added in the second, spiked sample solution of the first sample is to be detected at a retention time as shown in the second mass chromatogram;

d). running an image recognition algorithm to compare the first and second mass chromatograms of the first sample in order to determine whether a peak appears at the same retention time in the first mass chromatogram, and the peak in the first mass chromatogram has a shape substantially identical or similar to that of the peak of the first pesticide standard in the second mass chromatogram, and an intensity slightly smaller than that of the peak of the first pesticide standard;

if no, it is determined that the first sample contains no pesticide residue of the same kind as the first pesticide standard; and if yes, executing an image analysis to calculate an increased integral area (A1), representative for the concentration (X1) of the first pesticide standard, by which the peak of the second, spiked sample solution in the second mass chromatogram exceeds the peak of the first sample solution in the first mass chromatogram at the same retention time, and determining a concentration (Y1) of a pesticide residue in the first sample with the formula:

$$Y1=(A2/A1)X$$

where A2 is an integral area of the peak in the first mass chromatogram at the same retention time, A1 is the increased integral area, and X1 is the concentration of the first pesticide standard.

(e). after the injection of the first and second sample solutions of the first sample into the chromatographic and mass-spectrometric system, introducing the first and second sample solutions of the second sample consecutively into the chromatographic and mass-spectrometric system to create a first mass chromatogram for the first sample solution and a second mass chromatogram for the second, spiked sample solution, wherein a peak of the second pesticide standard added in the second, spiked sample solution of the second sample is to be detected at a retention time as shown in the second mass chromatogram;

f). running an image recognition algorithm to compare the first and second mass chromatograms of the second sample in order to determine whether a peak appears at the same retention time in the first mass chromatogram, and the peak in the first mass chromatogram has a shape substantially identical or similar to that of the peak of the second pesticide standard in the second mass chromatogram, and an intensity slightly smaller than that of the peak of the second pesticide standard;

if no, it is determined that the second sample contains no pesticide residue of the same kind as the second pesticide standard; and if yes, executing an image analysis to calculate an increased integral area (A3), representative for the concentration (X2) of the second pesticide standard, by which the peak of the second, spiked sample solution in the second mass chromatogram exceeds the peak of the first sample solution in the first mass chromatogram at the same retention time, and then determining a concentration (Y2) of a pesticide residue in the second sample with the formula:

$$Y2=(A4/A3)X2$$

where A4 is an integral area of the peak in the first mass chromatogram at the same retention time, A3 is the increased integral area, and X2 is the concentration of the second pesticide standard.

Preferably, the first pesticide standard added in the second, spiked sample solution of the first sample in step (a) and the second pesticide standard added in the second, spiked sample solution of the second sample in step (b) are of the same kind with the same concentration (X1, X2).

Preferably, the step (d) comprises the following steps:

(1). integrating a peak area of the first sample solution and a peak area of the second, spiked sample solution at the same retention time; and (2). subtracting the peak area of the first sample solution from the peak area of the second, spiked sample solution at the same retention time to get the increased integral area (A1).

Preferably, in step (c), the chromatographic and mass-spectrometric system is selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS).

Furthermore, the present invention provides a pesticide residue detection system, which generally includes a chromatographic and mass-spectrometric system and a computer. The chromatographic and mass-spectrometric system has an inlet for injection of a first sample solution and a second, spiked sample solution, which are prepared from two identical extracts of a sample with the first sample solution having no additives and the second, spiked sample solution having at least one pesticide standard of a known concentration (X) added. The computer is coupled to the chromatographic and mass-spectrometric system and is configured to create a first mass chromatogram for the first sample solution and a second mass chromatogram for the second, spiked sample solution, wherein a peak of the pesticide standard added in the second, spiked sample solution is to be detected at a retention time as shown in the second mass chromatogram. The computer is further configured to carry out an image recognition algorithm to compare the first and second mass chromatograms in order to determine whether a peak appears at the same retention time in the first mass chromatogram, and the peak in the first mass chromatogram has a shape substantially identical or similar to that of the peak of the pesticide standard in the second mass chromatogram, and an intensity slightly smaller than that of the peak of the pesticide standard. If no, it is determined that the sample contains no pesticide residue of the same kind as the pesticide standard; and if yes, the computer further executes an image analysis to calculate an increased integral area (A1), representative for the concentration (X) of the pesticide standard, by which the peak of the second, spiked sample solution in the second mass chromatogram exceeds the peak of the first sample solution in the first mass chromatogram at the same retention time, and then determines a concentration (Y) of a pesticide residue in the sample with the formula:

$$Y=(A2/A1)X$$

where A2 is an integral area of the peak in the first mass chromatogram at the same retention time, A1 is the increased integral area, and X is the concentration of the pesticide standard.

Preferably, the computer is configured to integrate a peak area of the first sample solution and a peak area of the second, spiked sample solution at the same retention time, and then to subtract the peak area of the first sample solution from the peak area of the second, spiked sample solution at the same retention time so as to get the increased integral area (A1), representative for the concentration of the pesticide standard.

Preferably, the chromatographic and mass-spectrometric system is selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS).

As described above, the first and second sample solutions are consecutively introduced in pairs into the chromatographic and mass-spectrometric system for analysis. While in between the two sample solutions, no other samples would be allowed to interfere in the chromatographic and mass-spectrometric system for test. This can greatly reduce any interferences caused by the sensitivity of the instrument. Additionally, the concentration of pesticide residue in a sample to be analyzed can be identified and measured through the use of a second, spiked sample solution in which a pesticide standard is intended to be added. Thus, unlike a conventional analytical method, there is no need to build a mass spectral database for interpretation of the pesticides or create a matrix-matched calibration curve for quantitative analysis. Most importantly, since the computer is utilized to analyze the data, no manpower is needed for interpretation of the pesticides and therefore the time needed for detecting the pesticide residues in agricultural products can be greatly shortened.

The foregoing and other objectives, features, and advantages of the invention will be more readily understood upon consideration of the following detailed description of the invention, taken in conjunction with the accompanying drawings.

DETAILED DESCRIPTION OF EMBODIMENTS

Figure 1:
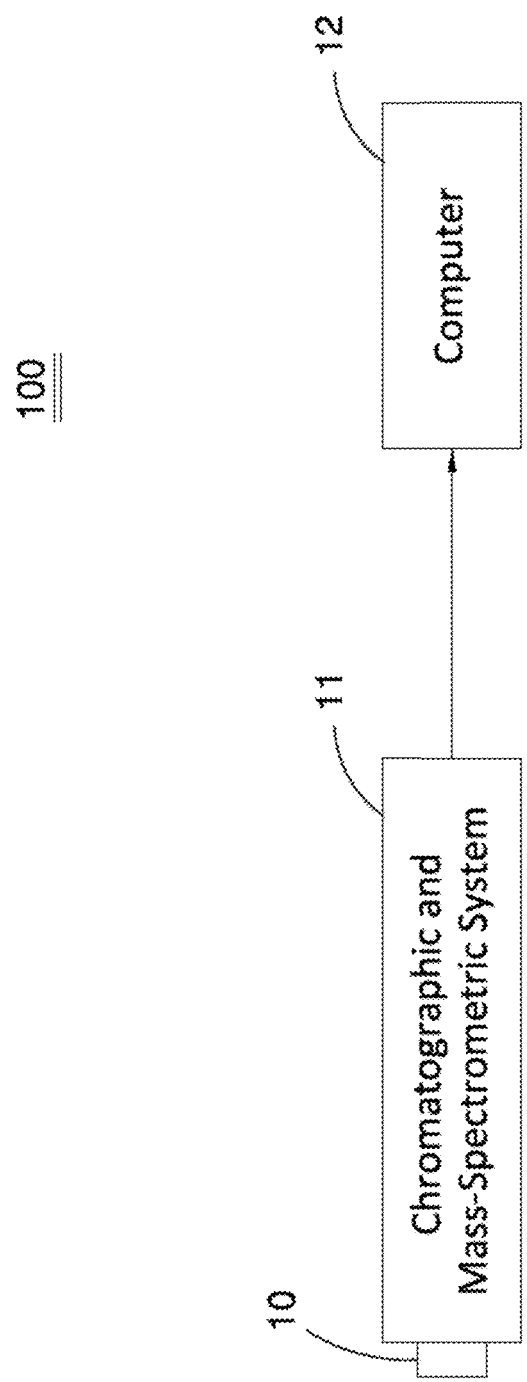
FIG. 1 is a block diagram of a pesticide residue detection system in accordance with the preferred embodiment of the present invention.
Figure 2:
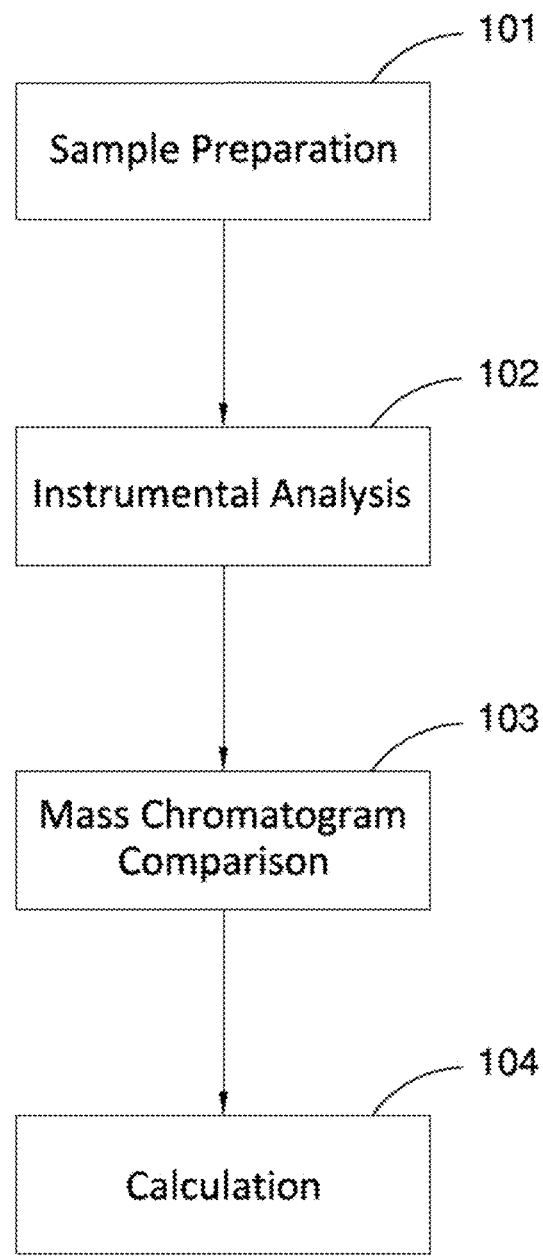
FIG. 2 is a flow diagram of the pesticide residue detection method in accordance with the preferred embodiment of the present invention.

Referring to FIGS. 1 and 2, there is shown a preferred embodiment of a pesticide residue detection system 100 and method. As shown in FIG. 1, the pesticide residue detection system 100 generally includes a chromatographic and mass-spectrometric system 11 and a computer 12 for performing the pesticide residue detection method. As shown in FIG. 2, the pesticide residue detection method generally includes the steps of sample preparation 101, instrumental analysis 102, mass chromatogram comparison 103 and calculation 104.

Firstly, in step 101, two identical extracts (Sample 1) are prepared, by a QuEChERS method for example, from a first sample to be analyzed, such as fruits, vegetables, etc. One of the two extracts directly serves as a first sample solution 1 with no additives while the other extract is added with at least one pesticide standard (STD) of a known concentration (X) to form a second, spiked sample solution 2. It should be noted that although the first sample solution 1 is not actively added with any additives (pesticides), the first sample solution 1 may has more or less pesticide residues because the original first sample to be analyzed itself may contain the pesticides.

Figure 3:
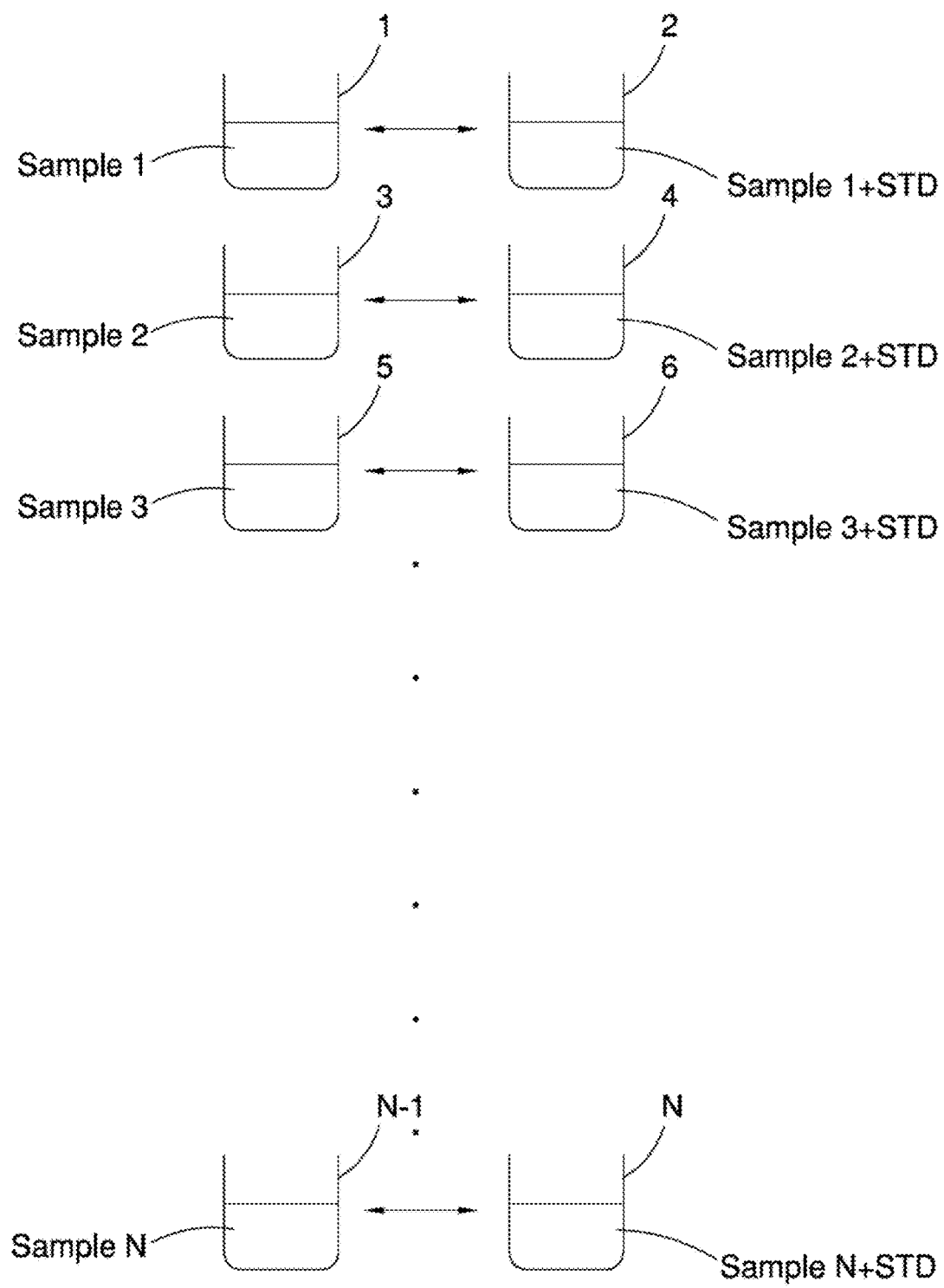
FIG. 3 depicts pairs of the first and second sample solutions prepared from different samples.

When many types or batches of agricultural products need to be examined, more samples to be analyzed are processed as in step 101 to form the sample solutions in pairs, as shown in FIG. 3. As shown, another two identical extracts (Sample 2) are prepared from a second sample to be analyzed, and one of which serves as a first sample solution 3 with no additives while the other extract is added with at least one pesticide standard (STD) of a known concentration (X) to form a second, spiked sample solution 4. Likewise, other two identical extracts (Sample 3) are prepared from a third sample to be analyzed, and one of which serves as a first sample solution 5 with no additives while the other extract is added with at least one pesticide standard (STD) of a known concentration (X) to form a second, spiked sample solution 6. The rest can be done in the same manner.

As described above, each pair of the sample solutions includes a first sample solution (1, 3, 5) with no additives and a second sample solution (2, 4, 6) added with the pesticide standard (STD). In practice, more than 310 types of known pesticides are mixed in advance to form a pesticide mixture standard solution and then added into the sample extract to form the second sample solution (2, 4, 6). Generally, if the instrument is set up well enough, each of the pesticides contained in each of the first and second sample solutions will come out at different retention times. The retention time difference can be used to distinguish one pesticide from another. Moreover, the multiple pesticides can further be double-checked or verified with a mass-spectrometer, such as direct analysis in real time/time-of-flight mass spectrometry (DART-TOF-MS). On the other hand, since there is no need in this present invention to make a matrix-matched calibration curve where a series of standard pesticides with different concentrations need to be prepared, the pesticide mixture standard solution to be added in the second, spiked sample solution of the each of the samples can be of the same kind with the same concentration, for the efficient and time saving sample preparation. For ease of explanation, only one known pesticide in the pesticide mixture standard solution will be described in detail later. That is, each of the second, spiked sample solution is added with one specific pesticide standard of a known concentration (X) in order to quantitatively determine if the original sample contains a pesticide residue of the same kind as the pesticide standard.

In step 102, the pairs of the first and second sample solutions are injected into an inlet 10 of the chromatographic and mass-spectrometric system 11 for analysis and to create a first mass chromatogram for the sample solution and a second mass chromatogram for the second, spiked sample solution. It is noted that either the first or the second sample solution can go first into the chromatographic and mass-spectrometric system 11 as long as the first and second sample solutions goes consecutively into the system 11. While in between the first and second sample solutions, there should be no other samples or reagents interfere in the system 11, thereby greatly reducing any interferences caused by the sensitivity of the instrument. If the instrument is set up well enough, a peak of the specific pesticide standard added in the second, spiked sample solution will come out and be detected at a specific retention time as shown in the second mass chromatogram. In practice, the chromatographic and mass-spectrometric system 11 may be selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS), etc.

In step 103, an image recognition algorithm is executed by the computer 12 to compare the first mass chromatogram of the first sample solution (Sample N) and the second mass chromatogram of the second, spiked sample solution (Sample N+STD) in order to identify and quantitate the pesticide residues in the sample, based on peak shape and peak intensity (or peak area).

More specifically, in step 103, when the first and second mass chromatograms are compared, the aim is to find out if a peak appears at the same retention time in the first mass chromatogram as in the second mass chromatogram, and the peak in the first mass chromatogram has a shape substantially identical or similar to that of the peak of the pesticide standard in the second mass chromatogram, and an intensity slightly smaller than that of the peak of the pesticide standard.

Take the first sample for example, if the first sample solution 1 and the second, spiked sample solution 2 of the first sample do not have their peaks sharing the same retention time, or the peak shapes not similar, or the peak intensities being extreme different, it is determined that the first sample contains no pesticide residue of the same kind as the pesticide standard. On the contrary, if a peak is found at the same retention time in the first mass chromatogram as in the second mass chromatogram, and the peak in the first mass chromatogram has a shape substantially identical or similar to that of the peak of the pesticide standard in the second mass chromatogram, and an intensity slightly smaller than that of the peak of the pesticide standard, then it is determined that the first sample solution 1 contains a pesticide of the same kind as the pesticide standard, and the peak area of the first sample solution 1 in the first mass chromatogram stands for a concentration (Y) of the pesticide residue in the sample. Likewise, since the second, spiked sample solution 2 is consisting of the original extract of the sample and the added pesticide standard, the peak area of the second, spiked sample solution 2 in the second mass chromatogram stands for the sum of the concentration (Y) of the pesticide residue in the sample plus the concentration (X) of the added pesticide standard.

Figure 5:
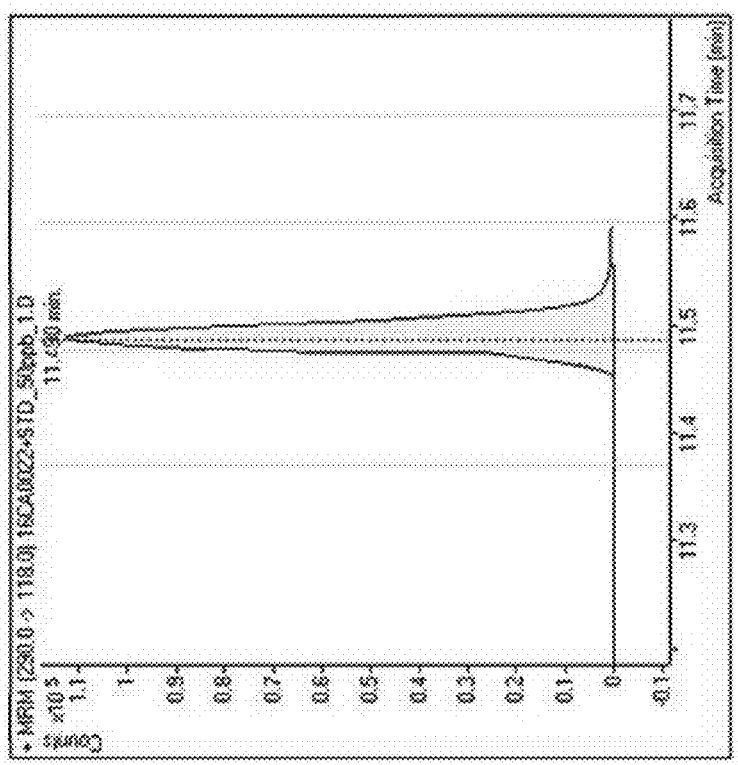
FIGS. 4 and 5 are mass chromatograms of the first and second sample solutions of a first sample.
Figure 4:
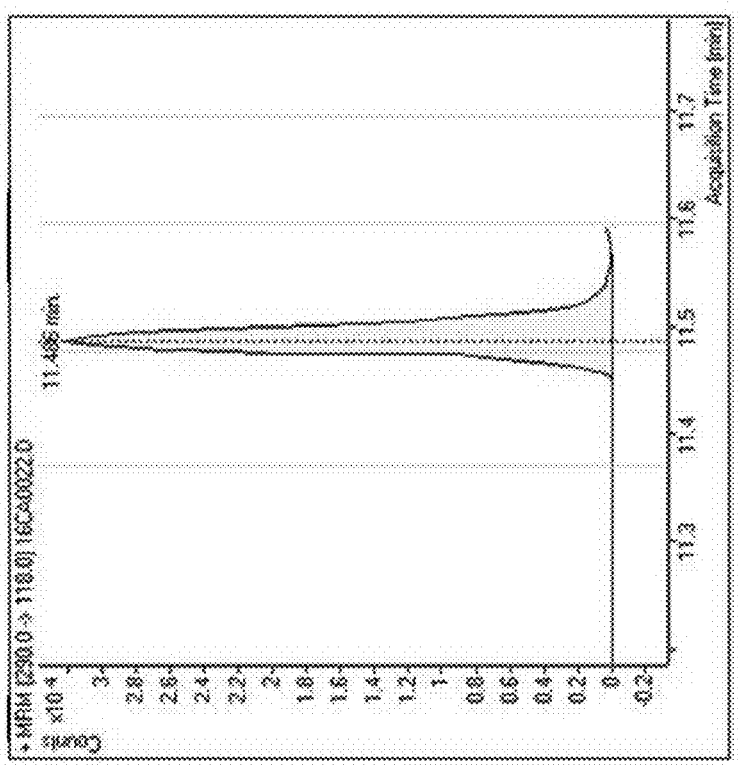

For instance, there are shown in FIG. 4 a first mass chromatogram of the first sample solution of a rice crop sample, and in FIG. 5 a second mass chromatogram of the second, spiked sample solution in which an isoprothiolane (pesticide standard) of a known concentration is added. A comparison of FIGS. 4 and 5 shows that at the retention time of about 11 minutes, there are shown two similar peaks in the respective first and second mass chromatograms, and the peak intensity in FIG. 5 is even slightly greater than the peak intensity in FIG. 4. Accordingly, the peak in FIG. 4 can be interpreted as a pesticide of the same kind as the added isoprothiolane. In other words, the rice crop sample has a pesticide residue of isoprothiolane.

As described above, the peak area of the first sample solution as in FIG. 4 is representative for the concentration (Y1) of the pesticide residue in the rice crop sample, and the peak area of the second, spiked sample solution as in FIG. 5 is representative for the sum of the concentration (Y1) of the pesticide residue in the rice crop sample plus the concentration (X1) of the added isoprothiolane. Most of all, the increased integral area, by which the peak of the second, spiked sample solution in the second mass chromatogram exceeds the peak of the first sample solution in the first mass chromatogram at the same retention time, is representative for the concentration (X1) of the added isoprothiolane.

Figure 6:
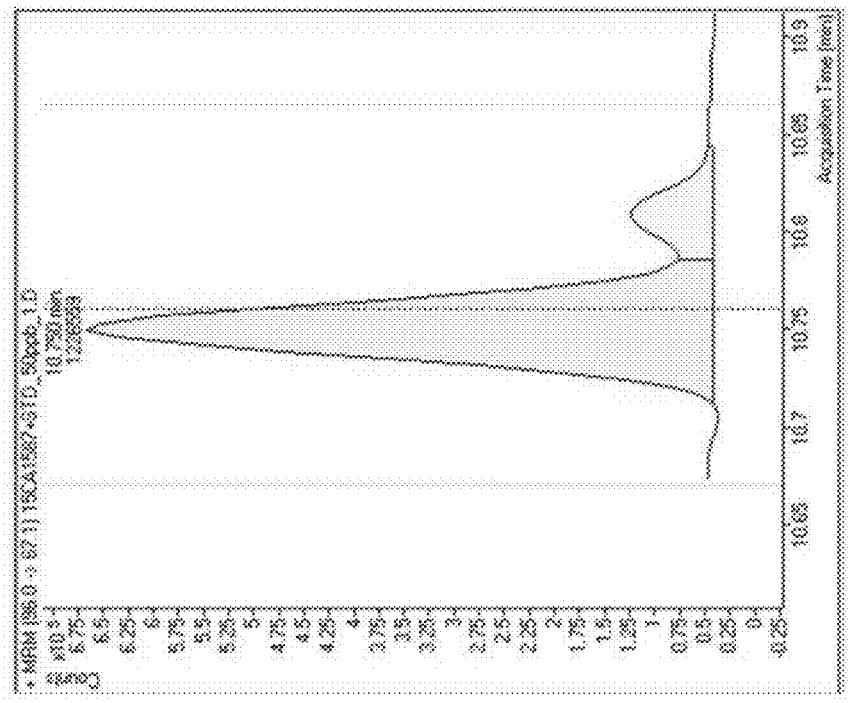
FIGS. 6 and 7 are mass chromatograms of the first and second sample solutions of a second sample.
Figure 7:
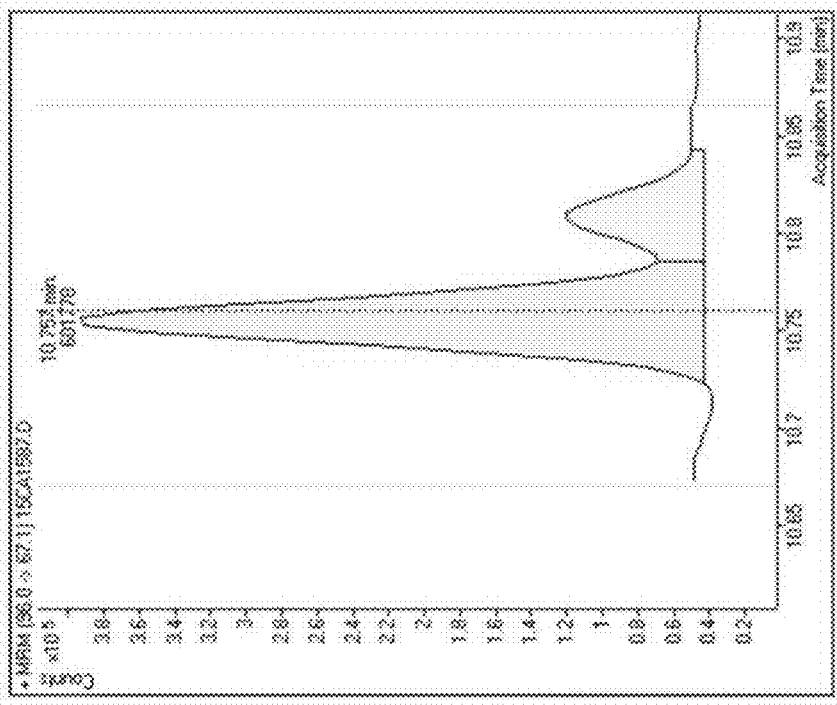

FIGS. 6 and 7 shows another example, in which it is found that two peaks of similar shapes appear at the same retention time in the respective mass chromatograms. By image analysis, it is determined that the intensity of the smaller peak on the right in FIG. 7 is actually not any greater than the smaller peak on the right in FIG. 6. Indeed, the two smaller peaks are almost the same in size. Accordingly, the smaller peak cannot be interpreted as a pesticide, but rather sample matrix or others, and thus can be ignored. On the other hand, the larger peak on the left in FIG. 7 is, however, higher than the larger peak on the left in FIG. 6. Accordingly, it can be interpreted to mean that the larger peak area on the left in FIG. 6 is directed to the concentration (Y2) of the pesticide residue in the sample, and the larger peak area on the left in FIG. 7 is directed to the sum of the concentration (Y2) of the pesticide residue in the sample plus the concentration (X2) of the added procymidone. And, the increased integral area, by which the peak on the left in FIG. 7 exceeds the peak on the left in FIG. 6 at the same retention time, is representative for the concentration (X2) of the added procymidone.

In step 104, the aim is to find out the concentration (Y) of the pesticide residue in the sample with all the data described above. Since the increased integral area is representative for the concentration (X) of the added pesticide standard, the concentration (Y) of the pesticide residue in the sample can be easily determined by the formula:

$$Y=(A2/A1)X$$

where A2 is an integral area of the peak in the first mass chromatogram at the same retention time, A1 is the increased integral area, and X is the concentration of the pesticide standard.

Preferably, the increased integral area A1 can be found by the following steps: Firstly, the peak area of the first sample solution and the peak area of the second, spiked sample solution at the same retention time are integrated separately. Then, the increased integral area (A1) can be obtained by subtracting the peak area of the first sample solution from the peak area of the second, spiked sample solution at the same retention time.

Incidentally, each pesticide has its own unique chemical and physical properties. Some can be detected at a really low concentration by the instrument for image analysis; however, others are not. They need to have a concentration high enough in order to be detected. Accordingly, in preparing the pesticide mixture standard solution (STD), all the known pesticides in the standard solution may have different concentrations as needed. Some are lower (10 ppb, for example), and others are higher (200 ppb). This ensures that all the pesticides can be detected by the instrument.

As described above, the first and second sample solutions are consecutively introduced in pairs into the chromatographic and mass-spectrometric system for analysis. While in between the two sample solutions, no other samples would be allowed to interfere in the chromatographic and mass-spectrometric system for test. This can greatly reduce any interferences caused by the sensitivity of the instrument. Additionally, the concentration of pesticide residue in a sample to be analyzed can be identified and measured through the use of a second, spiked sample solution in which a pesticide standard is intended to be added. Thus, there is no need to build a mass spectral database for interpretation of the pesticides or create a matrix-matched calibration curve for quantitative analysis. Most importantly, since the computer is utilized to analyze the data, no manpower is needed for interpretation of the pesticides and therefore the time needed for detecting the pesticide residues in agricultural products can be greatly shortened.

It should be evident that this disclosure is by way of example and that various changes may be made by adding, modifying or eliminating details without departing from the fair scope of the teaching contained in this disclosure.

What is claimed is:

1. A method for detecting pesticide residues, comprising:
   (a) preparing two identical extracts obtained from a sample to be analyzed, and turning one of the two extracts into a first sample solution with no additives, and the other extract to a second, spiked sample solution in which at least one pesticide standard of a known concentration (X) is added;
   (b) introducing the first and second sample solutions consecutively into a chromatographic and mass-spectrometric system to create a first mass chromatogram for the first sample solution and a second mass chromatogram for the second, spiked sample solution, wherein a peak of the pesticide standard added in the second, spiked sample solution is to be detected at a retention time as shown in the second mass chromatogram;
   c) running an image recognition algorithm to compare the first and second mass chromatograms in order to determine whether a peak appears at the same retention time in the first mass chromatogram, and the peak in the first mass chromatogram has a shape substantially identical or similar to that of the peak of the pesticide standard in the second mass chromatogram, and an intensity slightly smaller than that of the peak of the pesticide standard;
   if no, it is determined that the sample contains no pesticide residue of the same kind as the pesticide standard; and
   if yes, executing an image analysis to calculate an increased integral area (A1), representative for the concentration (X1) of the pesticide standard, by which the peak of the second, spiked sample solution in the second mass chromatogram exceeds the peak of the first sample solution in the first mass chromatogram at the same retention time, and then determining a concentration (Y) of a pesticide residue in the sample with the formula:

$$Y=(A2/A1)X$$

where A2 is an integral area of the peak in the first mass chromatogram at the same retention time, A1 is the increased integral area, and X is the concentration of the pesticide standard.

2. A method as recited in claim 1, wherein the step (c) comprises the following steps:
   (1) integrating a peak area of the first sample solution and a peak area of the second, spiked sample solution at the same retention time; and
   (2) subtracting the peak area of the first sample solution from the peak area of the second, spiked sample solution at the same retention time to get the increased integral area (A1).

3. A method as recited in claim 1, wherein in the step (b), the chromatographic and mass-spectrometric system is selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS).

4. A method for detecting pesticide residues, comprising:
   (a) preparing two identical extracts obtained from a first sample to be analyzed, and turning one of the two extracts into a first sample solution with no additives, and the other extract to a second, spiked sample solution in which at least one first pesticide standard of a known concentration (X1) is added;
   (b) preparing another two identical extracts obtained from a second sample to be analyzed, and turning one of the two extracts into a first sample solution with no additives, and the other extract to a second, spiked sample solution in which at least one second pesticide standard of a known concentration (X2) is added;
   (c) introducing the first and second sample solutions of the first sample consecutively into a chromatographic and mass-spectrometric system to create a first mass chromatogram for the first sample solution and a second mass chromatogram for the second, spiked sample solution, wherein a peak of the first pesticide standard added in the second, spiked sample solution of the first sample is to be detected at a retention time as shown in the second mass chromatogram;
   d) running an image recognition algorithm to compare the first and second mass chromatograms of the first sample in order to determine whether a peak appears at the same retention time in the first mass chromatogram, and the peak in the first mass chromatogram has a shape substantially identical or similar to that of the peak of the first pesticide standard in the second mass chromatogram, and an intensity slightly smaller than that of the peak of the first pesticide standard;

if no, it is determined that the first sample contains no pesticide residue of the same kind as the first pesticide standard; and if yes, executing an image analysis to calculate an increased integral area (A1), representative for the concentration (X1) of the first pesticide standard, by which the peak of the second, spiked sample solution in the second mass chromatogram exceeds the peak of the first sample solution in the first mass chromatogram at the same retention time, and then determining a concentration (Y1) of a pesticide residue in the first sample with the formula:

$$Y1=(A2/A1)X$$

where A2 is an integral area of the peak in the first mass chromatogram at the same retention time, A1 is the increased integral area, and X1 is the concentration of the first pesticide standard;

(e) after the injection of the first and second sample solutions of the first sample into the chromatographic and mass-spectrometric system, introducing the first and second sample solutions of the second sample consecutively into the chromatographic and mass-spectrometric system to create a first mass chromatogram for the first sample solution and a second mass chromatogram for the second, spiked sample solution, wherein a peak of the second pesticide standard added in the second, spiked sample solution of the second sample is to be detected at a retention time as shown in the second mass chromatogram;

f) running an image recognition algorithm to compare the first and second mass chromatograms of the second sample in order to determine whether a peak appears at the same retention time in the first mass chromatogram, and the peak in the first mass chromatogram has a shape substantially identical or similar to that of the peak of the second pesticide standard in the second mass chromatogram, and an intensity slightly smaller than that of the peak of the second pesticide standard;

if no, it is determined that the second sample contains no pesticide residue of the same kind as the second pesticide standard; and if yes, executing an image analysis to calculate an increased integral area (A3), representative for the concentration (X2) of the second pesticide standard, by which the peak of the second, spiked sample solution in the second mass chromatogram exceeds the peak of the first sample solution in the first mass chromatogram at the same retention time, and then determining a concentration (Y2) of a pesticide residue in the second sample with the formula:

$$Y2=(A4/A3)X2$$

where A4 is an integral area of the peak in the first mass chromatogram at the same retention time, A3 is the increased integral area, and X2 is the concentration of the second pesticide standard.

5. A method as recited in claim 4, wherein the first pesticide standard added in the second, spiked sample solution of the first sample in step (a) and the second pesticide standard added in the second, spiked sample solution of the second sample in step (b) are of the same kind with the same concentration.

6. A method as recited in claim 4, wherein the step (d) comprises the following steps:
 (1) integrating a peak area of the first sample solution and a peak area of the second, spiked sample solution at the same retention time; and
 (2) subtracting the peak area of the first sample solution from the peak area of the second, spiked sample solution at the same retention time to get the increased integral area (A1), representative for the concentration (X1) of the first pesticide standard.

7. A method as recited in claim 4, wherein in the step (c), the chromatographic and mass-spectrometric system is selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS).

8. A pesticide residue detection system, comprising:
 a chromatographic and mass-spectrometric system having an inlet for injection of a first sample solution and a second, spiked sample solution, which are prepared from two identical extracts of a sample with the first sample solution having no additives and the second, spiked sample solution having at least one pesticide standard of a known concentration (X) added;
 a computer coupled to the chromatographic and mass-spectrometric system and configured to create a first mass chromatogram for the first sample solution and a second mass chromatogram for the second, spiked sample solution, wherein a peak of the pesticide standard added in the second, spiked sample solution is to be detected at a retention time as shown in the second mass chromatogram; the computer further configured to carry out an image recognition algorithm to compare the first and second mass chromatograms in order to determine whether a peak appears at the same retention time in the first mass chromatogram, and the peak in the first mass chromatogram has a shape substantially identical or similar to that of the peak of the pesticide standard in the second mass chromatogram, and an intensity slightly smaller than that of the peak of the pesticide standard;
 if no, it is determined that the sample contains no pesticide residue of the same kind as the pesticide standard; and
 if yes, the computer further executes an image analysis to calculate an increased integral area (A1), representative for the concentration (X) of the pesticide standard, by which the peak of the second, spiked sample solution in the second mass chromatogram exceeds the peak of the first sample solution in the first mass chromatogram at the same retention time, and then determines a concentration (Y) of a pesticide residue in the sample with the foimula:

$$Y=(A2/A1)X$$

where A2 is an integral area of the peak in the first mass chromatogram at the same retention time, A1 is the increased integral area, and X is the concentration of the pesticide standard; and wherein the computer is configured to integrate a peak area of the first sample solution and a peak area of the second, spiked sample solution at the same retention time, and then to subtract the peak area of the first sample solution from the peak area of the second, spiked sample solution at the same retention time so as to get the increased integral area (A1).

9. A pesticide residue detection system as recited in claim 8, wherein the chromatographic and mass-spectrometric system is selected from the group consisting of liquid chromatography tandem mass spectrometry (LC-MS/MS), liquid chromatography-mass spectrometry (LC-MS), gas chromatography tandem mass spectrometry (GC-MS/MS), gas chromatography-mass spectrometry (GC-MS), direct analysis in real time/time-of-flight mass spectrometry (DART-TOF-MS), gas chromatography time-of-flight mass spectrometry (GC-TOF-MS), liquid chromatography time-of-flight mass spectrometry (LC-TOF-MS), gas chromatography/ion trap mass spectrometry (GC/ion trap MS), and liquid chromatography/ion trap mass spectrometry (LC/ion trap MS).

* * * * *